United States Patent [19]
Scarlett et al.

[11] Patent Number: 5,395,986
[45] Date of Patent: Mar. 7, 1995

[54] PROCESS FOR THE PRODUCTION OF CYCLOHEXANEDIMETHANOL

[75] Inventors: John Scarlett, Spennymoor; Michael A. Wood, Middlesbrough, both of England

[73] Assignee: Eastman Chemical Company, Kingsport, Tenn.

[21] Appl. No.: 174,314

[22] Filed: Dec. 30, 1993

[30] Foreign Application Priority Data

Dec. 2, 1993 [GB] United Kingdom ............... 9324784

[51] Int. Cl.$^6$ ............................................. C07C 31/27
[52] U.S. Cl. ................................. 568/831; 568/822; 568/830
[58] Field of Search ............... 568/822, 830, 831, 864

[56] References Cited

U.S. PATENT DOCUMENTS

| | | | |
|---|---|---|---|
| 2,040,944 | 5/1936 | Lazier | 568/844 |
| 2,079,414 | 5/1937 | Lazier | 568/830 |
| 2,091,800 | 8/1937 | Adkins et al. | 568/864 |
| 2,105,664 | 1/1938 | Lazier | 568/864 |
| 2,137,407 | 11/1938 | Lazier | 568/864 |
| 2,755,317 | 7/1956 | Kassel | 585/654 |
| 2,818,393 | 12/1957 | Lefrancois et al. | 502/100 |
| 2,830,095 | 4/1958 | Nicolaisen | 570/231 |
| 2,884,450 | 4/1959 | Holmquist | 568/880 |
| 2,901,466 | 8/1959 | Kibler et al. | 568/864 |
| 2,917,549 | 12/1959 | Hasek et al. | 568/830 |
| 3,334,149 | 8/1967 | Akin et al. | 568/830 |
| 4,032,458 | 6/1977 | Cooley et al. | 568/830 |

(List continued on next page.)

FOREIGN PATENT DOCUMENTS

143634 6/1985 European Pat. Off. .
241760 10/1987 European Pat. Off. .

(List continued on next page.)

OTHER PUBLICATIONS

Mansour et al., "Sel. Hydrog. of Esters to Alcoh. with a Catal. Obtained Rh$_2$O$_3$, Sn (n–C$_4$H$_9$)$_4$ and SiO$_2$ and Based On Isol. Active Centres", *Angew. Chem. 101*, (1989) Nr. 3, 360–63.
Wehner & Gustafson, "Catalytic Hydrog. of Esters Over Pd/ZnO", *Journ. of Catalysis*, 135, 420–426 (1992).
Lewin et al., "Fiber Chemistry", pp. 8–9 (1985).
Martyn V. Twigg, "Catalyst Handbook", 2nd Ed., p. 54.
Homer Adkins, "Catal. Hydrog. of Esters to Alcoh.", *Organic Reactions*, vol. 8, Chp. 1, pp. 2–27 (1954).
Freifelder, "Catal. Hydrog. in Org. Synth.", pp. 129–151.
Kirk–Othmer, *Encl. of Chem. Tech.*, 3rd Ed., vol. 1, pp. 733–739.

*Primary Examiner*—Werren B. Lone
*Attorney, Agent, or Firm*—J. Frederick Thomsen; Harry J. Gwinnell

[57] ABSTRACT

A process is described for the production of cyclohexanedimethanol having a trans-:cis-isomer ratio greater than about 1:1 by hydrogenation of a dialkyl (e.g. dimethyl) cyclohexanedicarboxylate having a trans-:cis-isomer ratio less than about 1:1 which comprises:

(a) providing a hydrogenation zone containing a charge of a granular heterogeneous ester hydrogenation catalyst;
(b) supplying to the hydrogenation zone a vaporous feed stream containing hydrogen and a hydrogenarable material comprising a dialkyl cyclohexanedicarboxylate at an inlet temperature which is above its dew point of the mixture;
(c) maintaining the hydrogenation zone under temperature and pressure conditions which are conducive to effecting hydrogenation of esters;
(d) passing the vaporous feed stream through the hydrogenation zone; and
(e) recovering from the hydrogenation zone a product stream containing cyclohexanedimethanol having a trans-:cis-isomer ratio greater than 1:1.

In this process it is preferred to use dimethyl 1,4-cyclohexanedicarboxylate to produce 1,4-cyclohexanedimethanol.

23 Claims, 5 Drawing Sheets

U.S. PATENT DOCUMENTS

| | | | |
|---|---|---|---|
| 4,052,467 | 10/1977 | Mills et al. | 568/880 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/864 |
| 4,751,334 | 6/1988 | Turner et al. | 568/864 |
| 4,837,368 | 6/1989 | Gustafson et al. | 568/881 |
| 4,929,777 | 5/1990 | Irick, Jr. et al. | 568/864 |
| 4,999,090 | 3/1991 | Tateno et al. | 203/36 |
| 5,030,771 | 7/1991 | Fuhrmann et al. | 568/830 |
| 5,124,435 | 6/1992 | Mori et al. | 528/307 |
| 5,142,067 | 8/1992 | Wegman et al. | 549/326 |
| 5,185,476 | 2/1993 | Gustafson | 568/831 |
| 5,191,091 | 3/1993 | Wegman et al. | 549/326 |

FOREIGN PATENT DOCUMENTS

| | | |
|---|---|---|
| 301853 | 2/1989 | European Pat. Off. |
| 353990 | 2/1990 | European Pat. Off. |
| 378756 | 7/1990 | European Pat. Off. |
| 552463 | 7/1993 | European Pat. Off. |
| 1276722 | 10/1961 | France |
| 1144703 | 3/1963 | Germany |
| 1159925 | 12/1963 | Germany |
| 2719867 | 11/1978 | Germany |
| 3843956 | 6/1990 | Germany |
| 4141199 | 6/1993 | Germany |
| 988316 | 4/1965 | United Kingdom |
| 1024318 | 3/1966 | United Kingdom |
| 1454440 | 11/1976 | United Kingdom |
| 1464263 | 2/1977 | United Kingdom |
| 2116552 | 9/1985 | United Kingdom |
| 2250287 | 6/1992 | United Kingdom |
| 8203854 | 11/1982 | WIPO |
| 8603189 | 6/1986 | WIPO |
| 8607358 | 12/1986 | WIPO |
| 8800937 | 2/1988 | WIPO |
| 8900886 | 2/1989 | WIPO |
| 9008121 | 7/1990 | WIPO |
| 9101961 | 2/1991 | WIPO |

PROCESS FOR THE PRODUCTION OF CYCLOHEXANEDIMETHANOL

FIELD OF THE INVENTION

This invention relates to a process for the production of cyclohexanedimethanol, and more particularly to a process for the production of a mixture containing a major amount of the trans-isomer of cyclohexanedimethanol and a minor amount of the corresponding cis-isomer.

BACKGROUND OF THE INVENTION 1,4-cyclohexanedimethanol is used to prepare highly polymeric linear condensation polymers by reaction with terephthalic acid and is useful as an intermediate in the preparation of certain polyester and polyester amides. The use of 1,4-cyclohexanedimethanol for such purposes is disclosed in, for example, U.S. Pat. No. 2,901,466. This document teaches that the trans-isomer of polycyclohexylenedimethylene terephthalate has a higher melting point range (315°–320° C.) than the corresponding cis-isomer (260°–267° C.).

One method for preparing 1,4-cyclohexanedimethanol (hexahydroterephthalyl alcohol) involves the hydrogenation of diethyl 1,4-cyclohexanedicarboxylate (diethyl hexahydroterephthalate) in a slurry phase reactor in the presence of a copper chromite catalyst at a pressure of 3000 psia (about 206.84 bar) and a temperature of 255° C., as is described in Example 3 of U.S. Pat. No. 2,105,664. The yield is said to be 77.5%.

The hydrogenation of dimethyl 1,4-cyclohexanedicarboxylate (DMCD) to 1,4-cyclohexanedimethanol (CHDM) is shown below in equation (1):

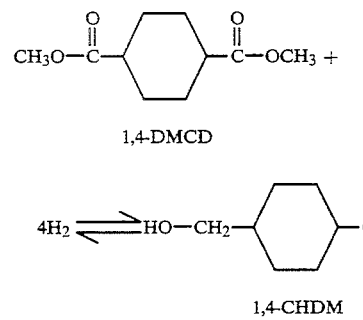

1,4-DMCD $4H_2 \rightleftharpoons HO-CH_2-\bigcirc-CH_2-OH + 2CH_3OH$ (1)

1,4-CHDM

The two geometrical isomers of CHDM thus produced are:

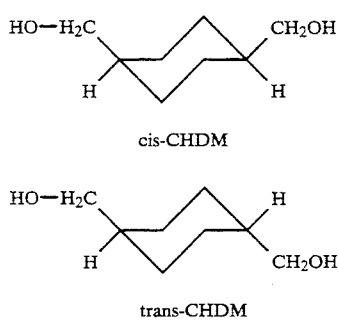

cis-CHDM trans-CHDM

The resulting 1,4-cyclohexanedimethanol product is a mixture of these two isomers which have different melting points. As reported on page 9 of the book "Fiber Chemistry" edited by Menachem Lewis and Eli M. Pearce, published by Marcel Dekker, Inc.: "Both the alicyclic ester [i.e. dimethyl 1,4-cyclohexanedicarboxylate] and the alicyclic diol [i.e.1,4-cyclohexanedimethanol] exist in two isomeric forms, cis . . . and trans . . . , that are not interconvertible without bond rupture". The passage continues later: "Control of the [cis-:trans-] ratio is important [in 1,4-cyclohexanedimethanol] since many polymer and fiber properties depend on it".

The cis-isomer of 1,4-cyclohexanedimethanol has a melting point of 43° C. and the trans has a melting point of 67° C. The higher melting point trans-isomer is often preferred over the cis-isomer for use as a reagent in the preparation of polyester and polyester-amides if a high melting point for such materials is considered desirable. As noted above, the trans-isomer of a typical polyester, such as trans-polycyclohexylmethyl terephthalate, has a higher melting point than the cis-isomer. Hence, for example, U.S. Pat. No. 5,124,435 discloses a polyester copolymer, the 1,4-cyclohexanedimethanol content of which has a trans-isomer content of at least 80 mole %, and which has a high heat resistance. The preferment of trans-1,4-cyclohexanedimethanol over cis-1,4-cyclohexanedimethanol is also discussed in U.S. Pat. No. 2,917,549, in U.S. Pat. No. 4,999,090 and in GB-A-988316.

A liquid phase process for the production of 1,4-cyclohexanedimethanol by plural stage hydrogenation of dimethyl terephthalate is described in U.S. Pat. No. 3,334,149. This utilises a palladium catalyst to effect hydrogenation of dimethyl terephthalate to dimethyl 1,4-cyclohexanedicarboxylate, followed by use of a copper chromite catalyst in the liquid phase to catalyse the hydrogenation of that diester to 1,4-cyclohexanedimethanol. In the procedure described in Example 1 of that patent specification a residence time of about 40 to 50 minutes is used in the second stage of this process.

In a liquid phase process for the production of 1,4-cyclohexanedimethanol, such as is disclosed in U.S. Pat. No. 3,334,149, the trans-:cis-isomer ratio of the product 1,4-cyclohexanedimethanol will tend towards an equilibrium value. This equilibrium value has been reported variously and may lie between about 2.57:1 (trans-:cis-1,4-cyclohexanedimethanol) (as reported in GB-A-988316) and about 3:1 (as reported in U.S. Pat. No. 2,917,549). However, the starting material, dimethyl 1,4-cyclohexanedicarboxylate, is generally commercially obtainable as a mixture of cis- and trans-isomers wherein there is a preponderance of the cis-isomer. Thus in a typical commercial grade of dimethyl 1,4-cyclohexanedicarboxylate the trans-:cis-isomer ratio is from about 0.5:1 to about 0.6:1.

Attempts to deal with the problem of the presence of an excess of the less desirable cis-1,4-cyclohexanedimethanol isomer in any process for 1,4-cyclohexanedimethanol manufacture have focused on the isomerisation of the cis-isomer of cyclohexanedimethanol to the trans-isomer thereof.

U.S. Pat. No. 2,917,549 discloses a process for isomerising cis-1,4-cyclohexanedimethanol to trans-1,4-cyclohexanedimethanol which comprises heating cis-1,4-cyclohexanedimethanol at a temperature of at least 200° C. in the presence of an alkoxide of a lower atomic weight metal such as lithium, sodium, potassium, calcium or aluminium. However, the process of U.S. Pat.

No. 2,917,549 necessarily involves a two-stage process wherein the initial cis-/trans- 1,4-cyclohexanedimethanol hydrogenation product is recovered from the hydrogenation zone and subjected to temperatures in excess of 200° C. in the presence of a metal alkoxide catalyst under an atmosphere of nitrogen. The capital and operational costs associated with a plant designed to carry out the process taught in U.S. Pat. No. 2,917,549 would be undesirably high. Another disadvantage of such a plant is the associated hazard relating to the use of metal alkoxides as catalysts in the isomerisation zone. Such catalysts are required to effect the isomerisation, which is reported not to occur under typical hydrogenation conditions using hydrogenation catalysts such as copper/chrome or Raney nickel catalysts, according to the teaching of Example 11 of U.S. Pat. No. 2,917,549. Furthermore, steps would be required to prevent product contamination by the metal alkoxide catalyst.

U.S. Pat. No. 4,999,090 discloses a process for the isomerisation of cis-1,4-cyclohexanedimethanol by distillation in the presence of an alkali metal hydroxide or alkoxide at a temperature of between 150° C. and 200° C. and at a pressure of between 1 mm Hg and 50 mm Hg (between 1.33 millibar and 66.5 millibar). This process has very similar disadvantages to those of U.S. Pat. No. 2,917,549.

GB-A-988316 teaches a process for the preparation of trans-1,4-cyclohexanedimethanol in which a mixture of cis- and trans-isomers of dimethyl hexahydroterephthalate (i.e. dimethyl 1,4-cyclohexanedicarboxylate) is hydrogenated at elevated temperature and pressure in the presence of a Cu/Zn catalyst. Trans-1,4-dimethylolcyclohexane (i.e. trans-1,4-cyclohexanedimethanol) is separated by crystallisation from the reaction product and then the residual product, now enriched in cis-1,4-cyclohexanedimethanol, is recycled to the hydrogenation zone whereupon it undergoes isomerisation to a cis-/trans- 1,4-cyclohexanedimethanol mixture. The recycle procedure may be repeated to obtain a 1,4-cyclohexanedimethanol product containing the trans-isomer in substantial excess. However, the process according to GB-A-988316 is more preferably operated under conditions such that recycled cis-isomer enriched product is combined with fresh dimethyl 1,4-cyclohexanedicarboxylate feed on re-entry to the hydrogenation zone. The effectiveness of recycling the cis-isomer to the hydrogenation zone is largely a result of the dual function of the copper/zinc catalyst which possesses both a hydrogenating and an isomerising catalytic action. As would be expected from thermodynamic principles, the isomerising action is most effective when a mixture containing a preponderance of the cis-isomer is recycled to the hydrogenation zone. However, recycling the cis-isomer in this way is acknowledged to cause a new problem, that of the formation of unwanted by-products, such as 1-methyl-4-hydroxymethylcyclohexane, which may be formed by operating the hydrogenation reaction under too severe conditions. To minimise the formation of such by-products, the hydrogenation zone may be operated under "relatively mild conditions", according to the teaching of GB-A-988316 (see, for example page 2, lines 55 to 79 of GB-A-988316). However, such mild conditions reduce the achieved conversion of dimethyl 1,4-cyclohexanedicarboxylate with the result that, for any one pass through the hydrogenation zone, a significant quantity of dimethyl hexahydroterephthalate (dimethyl 1,4-cyclohexanedicarboxylate) remains unconverted. By the term "relatively mild conditions" is meant a temperature of at least 200° C., preferably between 240° C. and 300° C., and a pressure of 200 to 300 atmospheres (202.65 bar to 303.98 bar), according to page 2, lines 26 to 32 of GB-A-988316. The use of such high pressures at these elevated temperatures can be hazardous, besides requiring reactors with thick walls and flanges of special alloy constructed to withstand such extreme pressures. Hence it is expensive to construct a plant to operate at pressures as high as envisaged in GB-A-988316. Furthermore it is potentially hazardous to operate a plant operating at 200 atmospheres (202.65 bar) or above, as well as being very expensive, not only in terms of the capital cost of the plant but also with regard to operating costs. A substantial proportion of this capital cost is associated with the rigorous safety precautions that must be taken when operating a high pressure conventional commercial scale hydrogenation plant. It is also expensive to compress gaseous streams to such high pressures and to circulate them through the plant.

Although there is a passing reference (see page 1, line 84 of GB-A-988316) to use of "the gaseous phase", even at temperatures of 300° C. both cis- and trans- dimethyl hexahydroterephthalate would be in the liquid phase at pressures of 200 to 300 atmospheres (202.65 bar to 303.98 bar) at the hydrogen:ester ratio envisaged in the Examples. Thus in each of the Examples of GB-A-988316 liquid phase conditions are used. According to Example 4, which uses a feed mixture containing dimethyl hexahydroterephthalate (i.e. 1,4-dimethyl cyclohexanedicarboxylate), and methanol such as might be used in a recycling process, the isomers present in the diol in the hydrogenation product are stated to represent an equilibrium mixture of about 72% of the trans- and about 28% of the cis-isomer, i.e. a trans-:cis-ratio of about 2.57:1.

It is known to effect hydrogenation of certain esters and diesters in the vapour phase. For example it has been proposed to use a reduced copper oxide/zinc oxide catalyst for effecting hydrogenation of esters in the vapour phase. In this connection attention is directed to GB-B-2116552. Also of relevance is WO-A-90/8121.

It is further known to produce diols, such as butane-1,4-diol, by catalytic hydrogenation of esters of dicarboxylic acids, such as a dimethyl or diethyl ester of maleic acid, fumaric acid, succinic acid, or a mixture of two or more thereof. Such processes are described, for example, in GB-A-1454440, GB-A-1464263, DE-A-2719867, U.S. Pat. No. 4,032,458, and U.S. Pat. No. 4,172,961.

Production of butane 1,4-diol by vapour phase hydrogenation of a diester, typically a dialkyl ester, of a $C_4$ dicarboxylic acid selected from maleic acid, fumaric acid, succinic acid, and a mixture of two or more thereof has been proposed. In such a process the diester is conveniently a di-$C_1$ to $C_4$ alkyl) ester, such as dimethyl or diethyl maleate, fumarate, or succinate. A further description of such a process can be found in U.S. Pat. No. 4,584,419, EP-A-0143634, WO-A-86/03189, WO-A-86/07358, and WO-A-88/00937.

In all of the above-mentioned vapour phase processes the esters or diesters all have a vapour pressure which is high compared to the vapour pressure of dimethyl 1,4-cyclohexanedicarboxylate and 1,4-cyclohexanedimethanol.

SUMMARY OF THE INVENTION

It is accordingly an object of the present invention to provide a process for the production of cyclohexanedimethanol by hydrogenation of a dialkyl cyclohexanedicarboxylate, for example dimethyl cyclohexanedicarboxylate, which can be operated with substantially increased safety and operating economy at relatively low pressures. Another object of the invention is to provide a process for production of cyclohexanedimethanol by hydrogenation of dimethyl cyclohexanedicarboxylate wherein the hydrogenation step yields directly a cyclohexanedimethanol product with a higher trans-:cis-isomer ratio than is reported to be achievable by conventional hydrogenation methods. Hence it is a still further object of the invention to avoid the increased capital and operating costs of the prior art processes mentioned above which require the use of extreme hydrogenation conditions or a separate isomerisation step. It is also an object of the present invention to provide a process wherein a mixture of cis- and trans-isomers of dimethyl 1,4-cyclohexanedicarboxylate is reacted rapidly with high conversion and high selectivity to a mixture of cis- and trans-isomers of 1,4-cyclohexanedimethanol wherein the trans-isomer is present in excess of the cis-isomer.

According to the present invention there is provided a process for the production of cyclohexanedimethanol having a trans-:cis -isomer ratio greater than about 1:1 by hydrogenation of a dialkyl cyclohexanedicarboxylate having a trans-:cis-isomer ratio less than about 1:1 which comprises:

(a) providing a hydrogenation zone containing a charge of a granular heterogeneous ester hydrogenation catalyst;

(b) supplying to the hydrogenation zone a vaporous feed stream of a mixture containing hydrogen and a hydrogenarable material comprising a dialkyl cyclohexanedicarboxylate at a feed temperature which is above the dew point of the mixture;

(c) maintaining the hydrogenation zone under temperature and pressure conditions which are conducive to effecting hydrogenation of esters;

(d) passing the vaporous feed stream through the hydrogenation zone; and (e) recovering from the hydrogenation zone a product stream containing cyclohexanedimethanol having a desired trans-:cis-isomer ratio greater than 1:1.

The invention is based upon the surprising discovery that, not only is the conversion of the starting material, i.e. dialkyl cyclohexanedicarboxylate, to the product, i.e. cyclohexanedimethanol, extremely rapid under the vapour phase hydrogenation conditions used, requiring only a matter of a few seconds for substantially complete conversion to occur, but also the isomerisation of cyclohexanedimethanol that occurs in passage through the hydrogenation zone is comparably rapid. This is a surprising finding since two separate reactions are involved. Thus a high trans-:cis- 1,4-cyclohexanedimethanol ratio typically greater than about 2.0:1 up to about 3.84:1, as well as essentially complete conversion of dialkyl 1,4-cyclohexanedicarboxylate to 1,4-cyclohexanedimethanol, can be achieved by using a residence time of less than about a minute of the reaction mixture in the hydrogenation zone, typically in the range of from about 2 to about 15 seconds. This residence time is in stark contrast to the extended residence times recommended in the prior art, such as the 40 to 50 minutes residence time used in Example 1 of U.S. Pat. No. 3,334,149.

The process of the invention is operated using vaporous feed conditions with the feed stream being supplied to the hydrogenation zone in essentially liquid free vaporous form. Hence the feed stream is supplied to the hydrogenation zone at an inlet temperature which is above the dew point of the mixture. The process can be operated so that vapour phase conditions will exist throughout the hydrogenation zone. However, when using dimethyl 1,4-cyclohexanedicarboxylate as starting material, the product, 1,4-cyclohexanedimethanol, is less volatile than the starting material, dimethyl 1,4-cyclohexanedicarboxylate, so that there is the possibility of condensation of a 1,4-cyclohexanedimethanol-rich liquid occurring on the catalyst, particularly if the temperature of the feed stream is close to its dew point. Such condensation of a 1,4-cyclohexanedimethanol-rich liquid on the catalyst is not deleterious in the process of the invention because the heat of hydrogenation of any dimethyl 1,4-cyclohexanedicarboxylate present in the 1,4-cyclohexanedimethanol-rich liquid can be dissipated by the heat sink effect of the 1,4-cyclohexanedimethanol. However, it is essential that the feed stream be at a feed temperature above its dew point at the inlet end of the catalyst bed if the advantage of vapour phase feed conditions is to be realised. The use of vapour phase feed conditions in the process of the invention has the advantage that, compared with liquid phase operation of the process, generally lower operating pressures can be used. This generally has a significant and beneficial effect not only on the construction costs but also on the operating costs of the plant.

In the hydrogenation zone the hydrogenatable material undergoes extremely rapid hydrogenation to yield cyclohexanedimethanol, as exemplified by equation (1) above. In addition, a comparably fast isomerisation reaction occurs under the hydrogenation conditions used. Hence a hydrogenatable material rich in cis-dimethyl cyclohexanedicarboxylate tends to yield a cyclohexanedimethanol product that has a higher content of the trans-isomer thereof than the trans-content of the starting ester.

In the case of hydrogenation of dimethyl 1,4-cyclohexanedicarboxylate we have found that the trans-:cis-isomer of the 1,4-cyclohexanedimethanol present in the reaction product mixture can be as high as approximately 3.84:1 under vapour phase hydrogenation conditions. This ratio is significantly higher than the ratio of between 2.57:1 and 3:1 which is reported to be achieved under liquid phase reaction conditions at low conversions.

In a preferred process the dialkyl cyclohexanedicarboxylate is a di-($C_1$ to $C_4$ alkyl) cyclohexanedicarboxylate, e.g. a dimethyl, diethyl, di-n- or -iso-propyl, or di-n-, -iso- or -sec-butyl cyclohexanedicarboxylate, more preferably dimethyl cyclohexanedicarboxylate. In an especially preferred process the dimethyl cyclohexanedicarboxylate is dimethyl 1,4-cyclohexanedicarboxylate.

In a particularly preferred process the dialkyl cyclohexanedicarboxylate is dimethyl 1,4-cyclohexanedicarboxylate and the product stream of step (e) comprises a 1,4-cyclohexanedimethanol product in which the trans-:cis-isomer ratio is in the range of from about 2:1 up to about 3.84:1, and is more preferably at least about 2.6:1 up to about 3.84:1. The process of the invention thus readily permits the preparation in a single step of a 1,4-cyclohexanedimethanol product in which the trans-:cis-isomer ratio is in excess of about 2:1 up to about 3.84:1, for example from about 2.6:1 to about 2.7:1. It is preferred that this ratio is at least about 2.6:1. The invention permits production in a single step of a 1,4-cyclohexanedimethanol product with a trans-:cis-isomer ratio of from about 3.1:1 up to about 3.84:1, e.g. about 3.2:1 up to about 3.7:1.

The hydrogenarable material supplied to the hydrogenation zone may comprise substantially pure cis-dimethyl cyclohexanedicarboxylate. However, it may further comprise trans-dimethyl cyclohexanedicarboxylate in addition to the cis-isomer thereof, provided that the trans-:cis-isomer ratio is less than 1:1. When the hydrogenarable material supplied to the hydrogenation zone comprises trans-dimethyl cyclohexanedicarboxylate, the molar ratio of trans-dimethyl cyclohexanedicarboxylate to cis-dimethyl cyclohexanedicarboxylate may be in the range of from about 0.01:1 to about 1:1, preferably in the range of from about 0.05:1 to about 1:1. Typically the molar ratio of the trans-isomer to the cis-isomer in the hydrogenatable material will be from about 0.5:1 to about 0.6:1 when the dimethyl cyclohexanedicarboxylate is the 1,4-isomer.

Whilst the process is used to advantage for the hydrogenation of dimethyl 1,4-cyclohexanedicarboxylate, it will be understood by those skilled in the art that the process of the invention may be equally well applied to the hydrogenation of any or all of dimethyl 1,2-cyclohexanedicarboxylate, dimethyl 1,3-cyclohexanedicarboxylate or dimethyl 1,4-cyclohexanedicarboxylate, and mixtures of two or more thereof.

In a preferred aspect of the present invention there is provided a vapour phase process for the production of cyclohexanedimethanol by hydrogenation of dimethyl cyclchexanedicarboxylate which comprises:
  (a) providing a hydrogenation zone containing a charge of a granular heterogeneous ester hydrogenation catalyst;
  (b) supplying to the hydrogenation zone a vaporous feed stream containing hydrogen and dimethyl cyclohexanedicarboxylate at an inlet temperature which is at or above the dew point of the mixture, wherein the dimethyl cyclohexanedicarboxylate is supplied to the hydrogenation zone at a rate corresponding to a liquid hourly space velocity of from about 0.05 to about 4.0 h$^{-1}$;
  (c) maintaining the hydrogenation zone at a combination of a temperature of from about 150° C. to 300° C. and a pressure of from about 150 psia (about 10.34 bar) to about 2000 psia (about 137.90 bar) which maintains both the dimethyl cyclohexanedicarboxylate reactant and the cyclohexanedimethanol product in the vapour phase; and
  (d) recovering from the hydrogenation zone a vaporous cyclohexanedimethanol product wherein the trans-:cis-isomer ratio of the cyclohexanedimethanol product is in the range of from about 2:1 to about 3.8:1.

The invention also provides a vapour phase process for the production of 1,4-cyclohexanedimethanol by hydrogenation of dimethyl 1,4-cyclohexanedicarboxylate which comprises:
  (a) providing a hydrogenation zone containing a charge of a granular heterogeneous ester hydrogenation catalyst;
  (b) supplying to the hydrogenation zone a vaporous feed stream containing hydrogen and dimethyl 1,4-cyclohexanedicarboxylate at an inlet temperature which is at or above the dew point of the mixture, wherein the dimethyl cyclohexanedicarboxylate is supplied to the hydrogenation zone at a rate corresponding to a liquid hourly space velocity of from about 0.2 to about 1.0 h$^{-1}$;
  (c) maintaining the hydrogenation zone at a combination of a temperature of from about 210° C. to about 260° C. and a pressure of from about 450 psia (about 31.03 bar) to about 1000 psia (about 68.95 bar) which maintains both the dimethyl 1,4-cyclohexanedicarboxylate reactant and the 1,4-cyclohexanedimethanol product in the vapour phase; and
  (d) recovering from the hydrogenation zone a vaporous 1,4-cyclohexanedimethanol product wherein the trans-:cis-isomer ratio of the 1,4-cyclohexanedimethanol product is in the range of from about 2.6:1 to about 3.8:1.

In the prior art hydrogenation of dimethyl cyclohexanedicarboxylate has normally been carried out as a high pressure, liquid phase process. It is surprising that, despite the relatively high molecular weight and low vapour pressure of dimethyl cyclohexanedicarboxylate at temperatures below those at which thermal decomposition is likely, e.g. below about 300° C., it is possible to design a viable commercial hydrogenation plant for hydrogenation of dimethyl cyclohexanedicarboxylate which utilises vapour phase feed conditions.

A surprising discovery is that the process of the invention can generate 1,4-cyclohexanedimethanol product mixtures whose trans-:cis-isomer ratio is in excess of the ratio that is the normal equilibrium ratio under liquid phase conditions. Thus, although the normal trans-:cis-isomer equilibrium ratio, under liquid phase conditions, can under favourable conditions be as high as about 3:1, the present invention, which operates with vaporous feed conditions, enables production of 1,4-cyclohexanedimethanol with a trans-:cis-isomer ratio as high as 3.84:1.

It is also surprising that the process of the invention can be operated for extended periods of up to several months or more, at high selectivity to the desired cyclohexanedimethanol product and at high conversion of the starting dialkyl cyclohexanedicarboxylate, since the prejudice in the art is that copper-containing catalysts would only have a short operating life and low activity at low operating pressures.

In the prior art it is made clear that the hydrogenation of dimethyl 1,4-cyclohexanedicarboxylate (dimethyl hexahydroterephthalate) is liable to give significant quantities of by-products. Thus GB-A-988316 acknowledges the problem caused by formation of unwanted by-products, such as 1-methyl-4-hydroxymethylcyclohexane. It is surprising to find that the process of the invention can be operated so that, despite the presence of a very large excess of hydrogen and the use of a very large vapour pressure of hydrogen compared to the relatively low vapour pressure of dimethyl cyclohexanedicarboxylate, the reaction proceeds rapidly with a very high conversion of dimethyl cyclohexanedicarboxylate to the desired product, i.e. cyclohexanedimethanol, but yet with a very high selectivity to that product and therefore with a very low yield of by-products. Thus under favourable conditions the conversion of dimethyl cyclohexanedicarboxylate to cyclohexanedimethanol can be as high as 98 mole % or higher with a selectivity to cyclohexanedimethanol of greater than 96 mole %. In addition it surprising to find that it is possible, under suitable reaction conditions, to convert a starting ester (dimethyl 1,4-cyclohexanedicarboxylate) that has a trans-:cis-isomer ratio less than 1:1 in a single step to a cyclohexanedimethanol product with a trans-:cis-isomer ratio that is greater than 1:1 and normally in the range of from about 2.6:1 up to as high as about 3.84:1, a value that is much higher than the highest equilibrium trans-:cis-isomer ratio that is disclosed in the prior art. It is further surprising to find that this can be accomplished at relatively low operating temperatures and pressures.

In a commercial plant the process will normally be operated on a continuous basis. It may be preferred to employ at least two hydrogenation zones, each containing a charge of a heterogeneous ester hydrogenation catalyst, connected in parallel. Each of these zones is capable of independent isolation from the supply of vaporous feedstock mixture. Hence an isolated zone may be subjected to conditions substantially different from those prevailing in the remaining zone or zones, for example, whereunder the catalyst charge therein may be reactivated or replaced whilst the process of the invention is continued in the remaining zone or zones. This arrangement also permits operation under the conditions taught in WO-A-91/01961. In this case two hydrogenation reactors connected in parallel are used. In a first phase of operation with a fresh charge of catalyst one only of the reactors is used, the other one being in standby mode with the catalyst bathed in hydrogen. After a period of operation over which the catalyst activity may decline somewhat the second reactor is used, whilst the first one is placed in standby condition. After a further period of operation both reactors are used in parallel until the time comes to replace the entire catalyst charge.

The process of the invention is normally operated at a feed temperature of at least about 150° C. and no higher than about 350° C. The feed temperature is preferably in the range of from about 150° C. to about 300° C., most preferably from about 200° C. to about 260° C.

The feed pressure typically is in the range of from about 150 psia (about 10.34 bar) up to about 2000 psia (about 137.90 bar). However, the benefits and advantages of the present low pressure, process utilising vaporous feed conditions are best realised by carrying out the process using a feed pressure of from about 450 psia (about 31.03 bar) up to about 1000 psia (about 68.95 bar).

The process requires that the vaporous feed stream is above its dew point so that the dialkyl (e.g. dimethyl) cyclohexanedicarboxylate is present in the vapour phase at the inlet end of the or each catalyst bed. This means that the composition of the vaporous feed mixture must be controlled so that, under the selected operating conditions, the temperature of the mixture at the inlet end of the or each catalyst bed is always above its dew point at the operating pressure. By the term "dew point" is meant that temperature at which a mixture of gases and vapours just deposits a fog or film of liquid. This dew point liquid will normally contain all the condensable components of the vapour phase, as well as dissolved gases, in concentrations that satisfy the usual vapour/liquid criteria. Typically the feed temperature of the vaporous feed mixture to the hydrogenation zone is from about 5° C. up to about 10° C. or more above its dew point at the operating pressure.

A convenient method of forming a vaporous mixture for use in the process of the invention is to spray liquid dialkyl (e.g. dimethyl) cyclohexanedicarboxylate or a dialkyl cyclohexanedicarboxylate solution into a stream of hot hydrogen-containing gas so as to form a saturated or partially saturated vaporous mixture. Alternatively such a vapour mixture can be obtained by bubbling a hot hydrogen-containing gas through a body of the liquid dialkyl cyclohexanedicarboxylate or dialkyl cyclohexanedicarboxylate solution. If a saturated vapour mixture is formed it should then be heated further or diluted with more hot gas so as to produce a partially saturated vaporous mixture prior to contact with the catalyst.

In the process of the invention the hydrogen-containing gas:dialkyl (e.g. dimethyl) cyclohexanedicarboxylate molar ratio can vary within wide limits, depending upon the temperature and pressure. Although the major constituent of the hydrogen-containing gas is hydrogen, other gases may also be introduced, normally in minor amount, in the hydrogen-containing gas supplied to the process, such as nitrogen, argon, methane, and carbon oxides. In order to maintain the vaporous feed stream above its dew point at the inlet end of the or each catalyst bed at the operating pressure the hydrogen-containing gas:dialkyl (e.g. dimethyl) cyclohexanedicarboxylate molar ratio is desirably at least about 10:1 up to about 8000:1, preferably in the range of from about 200:1 to about 1000:1. When using dimethyl 1,4-cyclohexanedicarboxylate as the diester starting material, it is not, however, necessary that the vaporous mixture in contact with all parts of the or each catalyst bed should be so far above its dew point as to prevent condensation of a 1,4-cyclohexanedimethanol-rich liquid. (Cyclohexanedimethanol is less volatile than the ester starting material, dimethyl 1,4-cyclohexanedicarboxylate).

The hydrogen-containing gas used in the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. For example, when using gas recycle, the gas recycle stream will normally contain minor amounts of an alkanol (e.g. methanol).

Although the process of the invention is operated with the feed stream in the vapour phase, it is convenient to express the feed rate of the hydrogenarable material to the hydrogenation zone as a space velocity and to express that space velocity as a liquid hourly space velocity. Hence it is convenient to express the feed rate in terms of the ratio of the liquid feed rate of the hydrogenarable material to the vaporisation zone to the volume of the hydrogenation catalyst. Thus the equivalent liquid hourly space velocity of the hydrogenarable material through the hydrogenation catalyst is preferably from about 0.05 to about 4.0 $h^{-1}$ In other words it is preferred to feed the liquid hydrogenarable material to the vaporisation zone at a rate which is equivalent to, per unit volume of catalyst, from about 0.05 to about 4.0 unit volumes of hydrogenatable material per hour (i.e. about 0.05 to about 4.0 $m^3 h^{-1}$ per $m^3$ of catalyst). Even more preferably the liquid hourly space velocity is from about 0.1 $h^{-1}$ to about 1.0 $h^{-1}$.

It will be readily apparent to those skilled in the art that the rate of passage of the vaporous feed stream through the hydrogenation zone will depend upon the feed rate of the hydrogenatable material to the vaporisation zone and upon the hydrogen-containing gas:hydrogenatable material molar ratio.

When using dimethyl 1,4-cyclohexanedicarboxylate feed there may be used any feedstock containing a significant quantity of cis-dimethyl 1,4-cyclohexanedicarboxylate and a trans-:cis- dimethyl 1,4-cyclohexanedicarboxylate isomer ratio of less than about 1:1. Suitable commercially available cis-rich grades of the feed ester dimethyl 1,4-cyclohexanedicarboxylate are high purity dimethyl 1,4-cyclohexanedicarboxylate, technical grade dimethyl 1,4-cyclohexanedicarboxylate, and cis-dimethyl 1,4-cyclohexanedicarboxylate. The preferred feedstock for the process of the invention is the technical grade dimethyl 1,4-cyclohexanedicarboxylate, as the high purity and cis-dimethyl 1,4-cyclohexanedicarboxylate requires additional purification stages to produce these grades.

The granular catalyst used in the process of the invention may be any catalyst capable of catalysing hydrogenation or hydrogenolysis of an ester to the corresponding alcohol or mixture of alcohols. It may be formed into any suitable shape, e.g. pellets, rings or saddles.

Typical ester hydrogenation catalysts include copper-containing catalysts and Group VIII metal-containing catalysts. Examples of suitable copper-containing catalysts include reduced copper-on-alumina catalysts, reduced copper oxide/zinc oxide catalysts, with or without a promoter, reduced manganese promoted copper catalysts, and reduced copper chromite catalysts, with or without a promoter, while suitable Group VIII metal catalysts include platinum catalysts and palladium catalysts. Suitable copper oxide/zinc oxide catalyst precursors include CuO/ZnO mixtures wherein the Cu:Zn weight ratio ranges from about 0.4:1 to about 2:1. An example is the catalyst precursor bearing the designation DRD 92/71. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor available under the designation DRD 92/92. Suitable copper chromite catalyst precursors include those wherein the Cu:Cr weight ratio ranges from about 0.1:1 to about 4:1, preferably from about 0.5:1 to about 4:1. Catalyst precursors of this type are the precursors available under the designation DRD 89/21 or under the designation PG 85/1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89.

All of the above mentioned catalysts available under the general designations DRD or PG can be obtained from Davy Research and Development Limited, P.O. Box 37, Bowesfield Lane, Stockton-on-Tees, Cleveland TS18 3HA, England.

Other catalysts which can be considered for use include Pd/ZnO catalysts of the type mentioned by P. S. Wehner and B. L. Gustafson in Journal of Catalysis 136, 420–426 (1992), supported palladium/zinc catalysts of the type disclosed in U.S. Pat. No. 4,837,368 and U.S. Pat. No. 5,185,476, and chemically mixed copper-titanium oxides of the type disclosed in U.S. Pat. No. 4,929,777.

Further catalysts of interest for use in the process of the invention include the rhodium/tin catalysts reported in A. El Mansour, J. P. Candy, J. P. Bournonville, O. A. Ferrehi, and J. M Basset, Angew. Chem. 101, 360 (1989).

Any recognised supporting medium may be used to provide physical support for the catalyst used in the process of the invention. This support can be provided by materials such as zinc oxide, alumina, silica, alumina-silica, silicon carbide, zirconia, titania, carbon, a zeolite, or any suitable combination thereof.

The catalysts that are particularly preferred for use in the process of the invention are the reduced forms of the copper chromite, promoted copper chromite, and manganese promoted copper catalyst precursors described hereinabove.

According to one preferred procedure the process of the invention is carried out using at least two hydrogenation reactors connected in parallel, each zone containing a respective charge of the hydrogenation catalyst. The vaporous feed stream may, in a first phase of operation with a fresh catalyst charge, be supplied to one reactor only whilst the second reactor is in standby mode and then, in a second phase of operation, be supplied to the second reactor whilst the first reactor is in standby mode. In each of these first two phases the initially fresh catalyst charge in the respective reactor will become somewhat deactivated. In a third phase of operation the vaporous feed mixture is supplied to both reactors simultaneously, as taught in WO-A-91/01961. In this way the effective life of the total catalyst charge can be extended.

It is also contemplated to use a hydrogenation zone which comprises two or more hydrogenation reactors connected in series.

The or each hydrogenation zone may comprise a shell-and-tube reactor which may be operated under isothermal, or near isothermal, conditions with the catalyst in the tubes and the coolant in the shell or vice versa. Usually, however, it will be preferred to use adiabatic reactors since these are cheaper to construct and install than shell-and-tube reactors. Such an adiabatic reactor may contain a single charge of a hydrogenation catalyst or may contain two or more beds of catalyst, or beds of different hydrogenation catalysts. If desired, external or internal inter-bed heat exchangers may be provided in order to adjust the inlet temperature to one or more beds of catalyst downstream from the inlet to the adiabatic hydrogenation reactor.

In an alternative procedure the plant includes at least two hydrogenation zones, each containing a charge of granular hydrogenation catalyst, and the vaporous feed stream is supplied to at least one of the hydrogenation zones, in a first phase of operation, while at least one other hydrogenation zone is supplied with a stream of hydrogen-containing gas thereby to reactivate the charge of hydrogenation catalyst therein. In a second phase of operation the at least one other hydrogenation zone is supplied with the vaporous feed stream while the at least one hydrogenation zone is supplied with a stream of hydrogen-containing gas thereby to reactivate the charge of hydrogenation catalyst therein.

In this procedure the or each hydrogenation zone that is not on line is supplied with a stream of hydrogen-containing gas thereby to reactivate the catalyst charge. Normally it will be preferred to carry out this reactivation at elevated temperature, typically at a temperature of about 100° C. or more up to about 350° C. In this reactivation step the inlet temperature to the respective hydrogenation zone or zones may be lower than, e.g. about 10° C. to about 50° C. lower than, substantially equal to, or higher than, e.g. about 10° C. to about 50° C. higher than, the feed temperature of the vaporous feed stream to the on line hydrogenation zone or zones. The stream of hydrogen-containing gas used in such a reactivation step may comprise a hot stream of recycle and make-up gas.

In one form of this alternative procedure there is recovered from the zone or zones undergoing reactivation of the catalyst a stream of hydrogen-containing gas which is admixed with a vaporous hydrogen-containing stream of the dialkyl (e.g. dimethyl) cyclohexanedicarboxylate to form the vaporous feed stream to the on line zone or zones. In another form there is recovered from the zone or zones whose catalyst is undergoing reactivation a stream of hydrogen-containing gas which is admixed with the reaction product stream from the on line zone or zones. In a still further form of this alternative procedure there is recovered from the zone or zones undergoing catalyst reactivation a stream of hydrogen-containing gas which is used to vaporise the dialkyl (e.g. dimethyl) cyclohexanedicarboxylate to form a vaporous hydrogen-containing stream of the dialkyl cyclohexanedicarboxylate. It is further convenient to form the vaporous feed stream to the on line zone or zones by admixing hot recycle gas with a vaporous hydrogen-containing stream of dialkyl (e.g. dimethyl) cyclohexanedicarboxylate. The direction of flow of the stream of hydrogen-containing gas through the or each hydrogenation zone in which catalyst reactivation is occurring may be the same as, or opposite to, the direction of flow of the vaporous feed stream through that zone when it is on line.

DETAILED DESCRIPTION OF THE PREFERRED EMBODIMENTS

It will be understood by those skilled in the art that FIGS. 1 to 4 of the drawings are diagrammatic and that further items of equipment such as temperature and pressure sensors, pressure relief valves, control valves, level controllers and the like would additionally be required in a commercial plant. The provision of such ancillary items of equipment forms no part of the present invention and would be in accordance with conventional chemical engineering practice. Moreover it is not intended that the scope of the invention should be limited in any way by the precise methods of heating, vaporising and condensing various process streams or by the arrangement of heaters, heat exchangers, vaporising or condensing apparatus provided therefor. Any suitable arrangement of equipment other than that depicted in FIGS. 1 to 4 which fulfils the requirements of the invention may be used in place of the illustrated equipment in accordance with conventional chemical engineering techniques.

Figure 1:
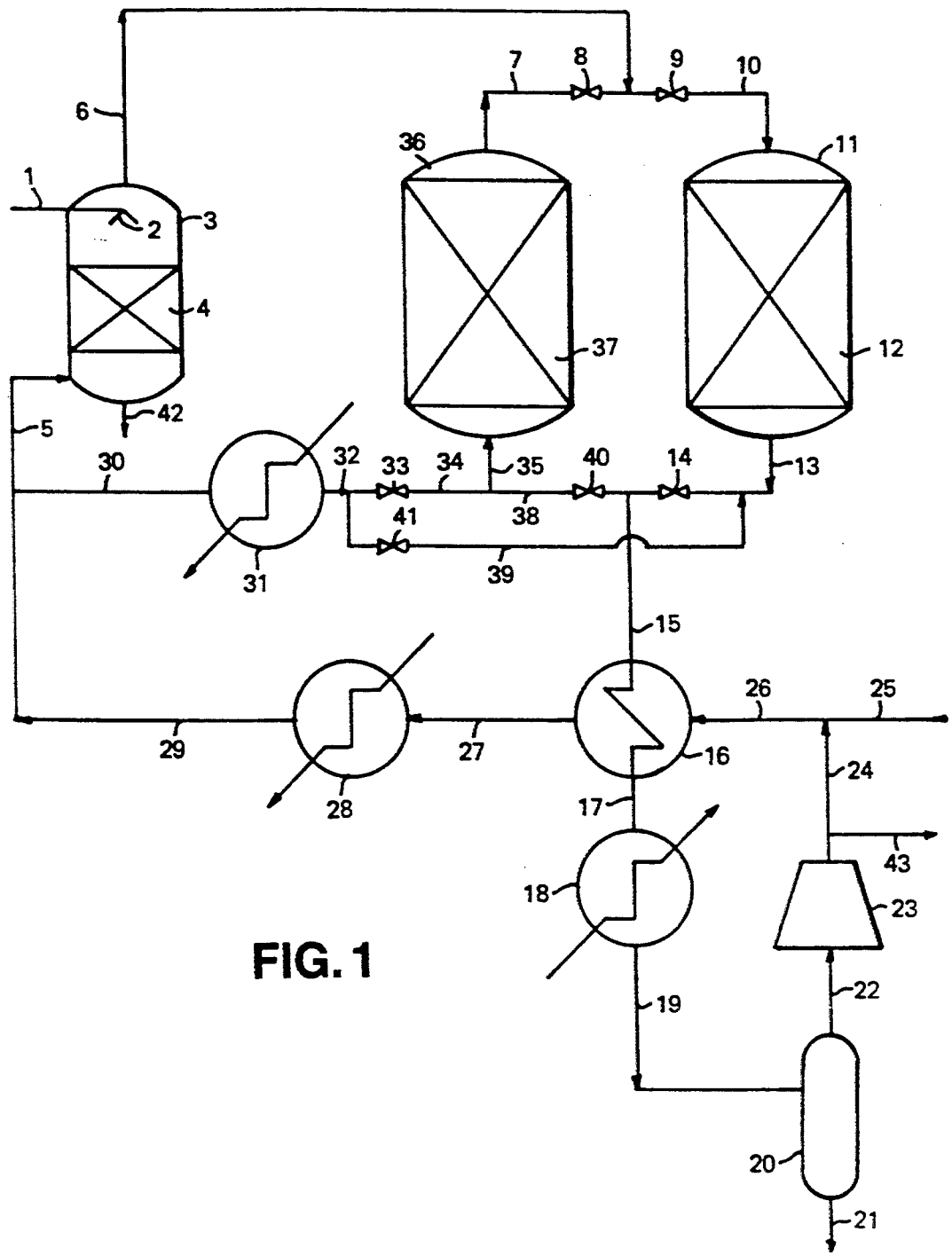
FIGS. 1 to 4 are each a simplified flow diagram of a plant for production of 1,4-cyclohexanedimethanol in two hydrogenation reactors connected in parallel by hydrogenation of dimethyl 1,4-cyclohexanedicarboxylate.

Referring to FIG. 1 of the drawings, a technical grade of dimethyl 1,4-cyclohexanedicarboxylate is supplied in line 1, in a first phase of operation, to a vaporiser nozzle 2 located in an upper part of a vaporiser vessel 3 above a bed of packing 4. A stream of hot hydrogen-containing gas is supplied to the bottom of vaporiser vessel 3 in line 5. A saturated vaporous mixture comprising dimethyl 1,4-cyclohexanedicarboxylate is recovered in line 6 from the top of vaporiser vessel 3. The resulting vaporous mixture is mixed with further hot hydrogen-containing gas from line 7 under the control of valve 8. The combined stream which now has a hydrogen:dimethyl 1,4-cyclohexanedicarboxylate molar ratio of 400:1 and is at a pressure of about 63 bar and at a temperature of about 230° C., is fed by way of valve 9 and line 10 to a hydrogenation reactor 11 which contains a bed of a pelleted heterogeneous hydrogenation catalyst 12, such as reduced copper chromite or the chromium-free catalyst designated DRD92/89. The hydrogenation reaction product mixture exits reactor 11 via line 13 and passes through valve 14 to enter line 15. The hydrogenation reaction product mixture in line 15 is cooled in heat interchanger 16 and the resulting partially condensed mixture passes on in line 17 through cooler 18 in which it is further cooled. The resulting mixture of gas and condensate flows on in line 19 to a gas-liquid separator 20 from which a mixture of methanol and crude 1,4-cyclohexanedimethanol is recovered in line 21. The uncondensed gaseous mixture in line 22 comprises unreacted hydrogen together with inert gases and methanol vapour and is compressed by means of compressor 23 to give a compressed gas stream in line 24.

The compressed recycled gas in line 24 is combined with make-up hydrogen-containing gas from line 25. The combined mixture in line 26 is heated by passage through heat exchanger 16 and flows on in line 27 to heater 28 in which its temperature is raised further to a suitable temperature for effecting vaporisation of the dimethyl 1,4-cyclohexanedicarboxylate feed. The resulting hot gas in line 29 is then divided into two streams, one being the stream in line 5 and the other being a stream in line 30. This latter stream is heated further in heater 31 to a temperature of about 240° C.

and passes on by way of line 32, valve 33 and lines 34 and 35 to the bottom end of a second hydrogenation reactor 36 which, in this first phase of operation, is in reactivation mode. Reactor 36 contains a charge of hydrogenation catalyst 37. The hot gas exiting the top of reactor 36 in line 7 is admixed, as already described above, with the saturated vaporous mixture in line 6 to increase the hydrogen:dimethyl 1,4-cyclohexanedicarboxylate molar ratio therein and to raise its temperature above its dew point, e.g. at least 5° C. to 10° C. above its dew point.

The plant also includes lines 38 and 39 and valves 40 and 41 both of which are closed in this phase of operation. Line 42 indicates a line by means of which a stream containing any "heavies" collecting in the bottom of vaporiser vessel 3 can be drawn off. Reference numeral 43 indicates a purge gas line through which a purge gas stream can be taken in order to limit the build up of inert gases in the circulating gas. Such inert gases may enter the plant in the make up gas stream in line 25.

After a period of operation the activity of the catalyst charge 12 will have declined to a point at which reactivation is desirable. Although the reasons for catalyst deactivation have not been clarified, it can be postulated that a possible cause of this loss of catalyst activity is the formation of traces of involatile polyesters on the catalyst surface due to ester exchange reactions between, for example, dimethyl 1,4-cyclohexanedicarboxylate, on the one hand, and 1,4-cyclohexanedimethanol, or methyl 4-hydroxymethylcyclohexanecarboxylate, which can be postulated to be an intermediate product of the hydrogenation reaction, or hydroxymethylcyclohexylmethyl 1,4-cyclohexanedicarboxylate, which is the ester interchange product between dimethyl 1,4-cyclohexanedicarboxylate and 1,4-cyclohexanedimethanol, on the other hand. The resulting di- or trimeric materials can then undergo further reaction with components of the vaporous mixture to cause these oligomeric chains to grow. Polyethers and mixed polyethers-polyesters can also be formed.

Such polymeric by-products on the catalyst surface are susceptible to hydrogenation. Hence reactivation of the catalyst by treatment with a hot hydrogen-containing gas is possible. It has further been shown in the course of experimental work to investigate the hydrogenation of dimethyl 1,4-cyclohexanedicarboxylate which forms the background to the present invention that, for whatever reason, the passage of a hot stream of hydrogen-containing gas over partially deactivated catalyst has a beneficial effect in at least partially restoring the activity of the catalyst.

Accordingly in a second phase of operation valve 33 is shut and valve 41 is opened, while valve 14 is closed and valve 40 is opened. In this way hydrogenation reactor 36 with its fresh or reactivated catalyst charge 37 is brought on line, whilst reactor 11 goes into reactivation mode and its partially deactivated charge of catalyst 12 is reactivated. In this second mode of operation the saturated vaporous mixture in line 6 is mixed with hot hydrogen-containing gas from line 10 to form a vaporous feed mixture which flows in line 7 through reactor 36 and its catalyst charge 37. The resulting reaction mixture passes by way of lines 35 and 38 through valve 40 to line 15. The hot hydrogen-containing gas from line 32 passes through valve 41 to line 39 and then through line 13 to the bottom of hydrogenation reactor 11.

When the catalyst charge 37 has become deactivated to some extent the valves 14, 33, 40 and 41 can be readjusted to switch the flows through hydrogenation reactors 11 and 36 back to those of the first phase of operation.

The above described steps can be repeated as often as may be expedient, bringing the reactors 11 and 36 on line in turn until the reactivation procedure no longer results in the desired increase in catalyst activity or until the plant has to be shut down for maintenance or other reasons, whereupon the catalyst charges 12 and 37 can be discharged and replaced by fresh charges of catalyst or catalyst precursor.

The make-up gas in line 25 can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired.

At start up of the plant the reactors 11 and 36 are each charged with a charge of a heterogeneous hydrogenation catalyst precursor, such as a copper chromite catalyst precursor. Preferably, however, the reactors 11 and 36 are charged with a chromium-free hydrogenation catalyst, such as DRD92/89. The catalyst precursor is then reduced carefully following the catalyst supplier's instructions. If the process of EP-A-0301853 is used to reduce a copper chromite precursor, then both beds of catalyst 12 and 37 can be reduced simultaneously. In other cases it may be expedient to reduce the beds 12 and 37 separately. After pre-reduction of the catalyst precursor hot hydrogen-containing gas is circulated through the plant. When the appropriate inlet temperatures to vaporiser vessel 3 and to reactor 11 have been achieved the flow of dimethyl 1,4-cyclohexanedicarboxylate in line 1 is commenced to bring the plant on line in the first phase of operation.

Figure 2:
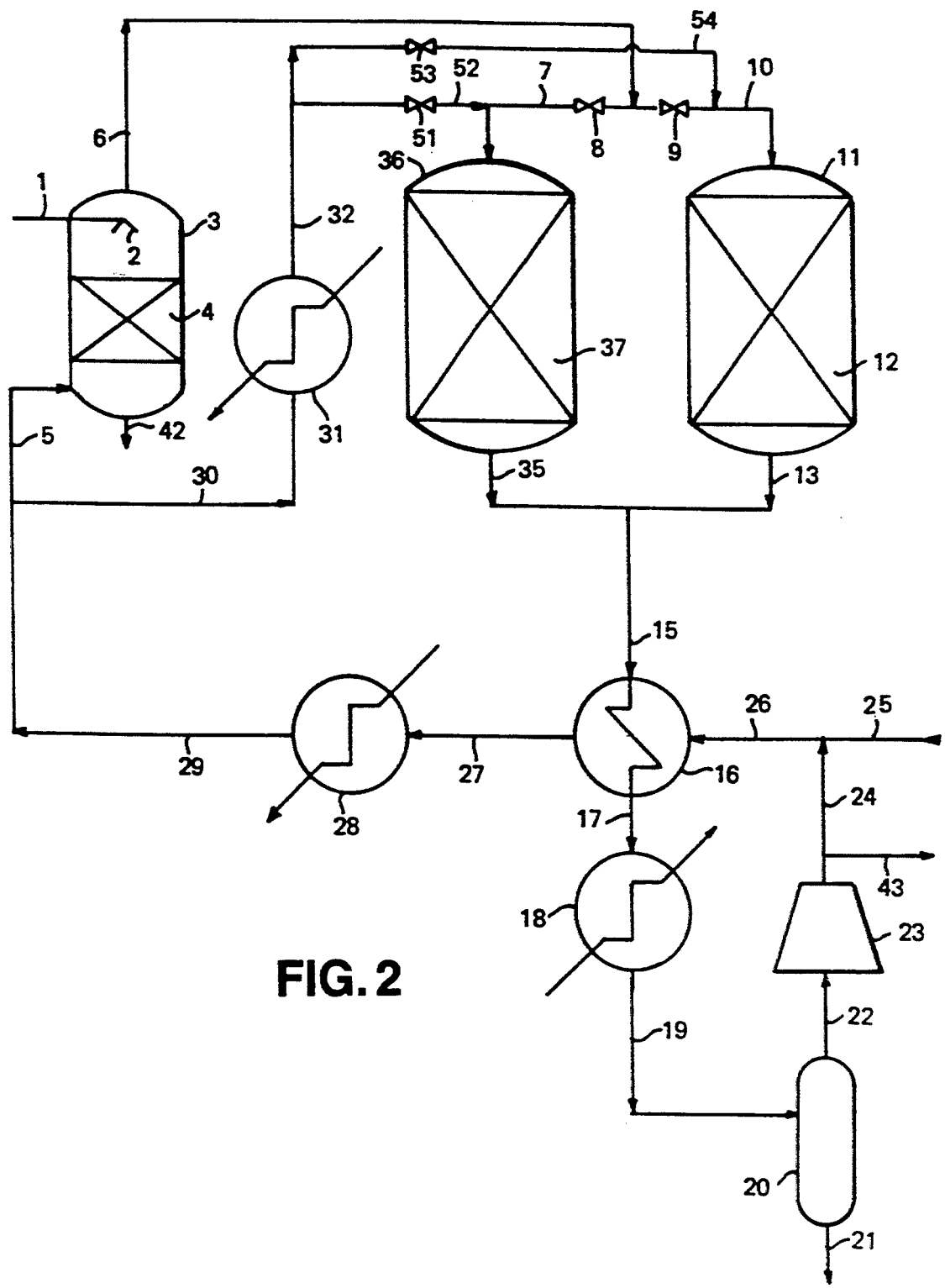

In FIG. 2 of the drawings the same reference numerals have been used as in FIG. 1 to denote like items of equipment. Whereas the hydrogen-containing gas flows in the plant of FIG. 1 through the catalyst bed 12 or 37 in the opposite direction during the reactivation mode from the direction of flow of the vaporous feed stream through the same bed 12 or 37 in the on line mode, in the plant of FIG. 2 the direction of gas flow during the catalyst reactivation mode and that during the on line mode through a particular bed 12 or 37 are the same in each case.

In the plant of FIG. 2 hot gas from the stream in line 32 can be fed either via valve 51 and line 52 into line 7 and then through reactor 36 or via valve 53 and line 54 into line 10 and then through reactor 11. If reactor 11 is in on line mode with valve 8 closed and reactor 36 is in reactivation mode, then valve 51 is adjusted so that most Of the gas from line 32 flow through valve 51 into reactor 36 and only sufficient gas passes through valve 53 into line 10 to raise the inlet temperature to reactor 11 above its dew point. To bring reactor 36 into on line mode valve 9 is closed and valve 8 is opened, whereupon valve 51 is closed somewhat and valve 53 is opened a corresponding amount to cause most of the gas from line 32 to flow through reactor 11 while only sufficient gas passes through valve 51 to satisfy dew point requirements.

In the plant of FIG. 2 any volatile potential catalyst deactivating materials released in the reaction mode do not pass through the on line catalyst charge and can be recovered in the product stream in line 21. Although preliminary indications are that no such catalyst deactivating materials are released when the unsaturated organic compound being hydrogenated is dimethyl 1,4-cyclohexanedicarboxylate, this may not be the case when other unsaturated organic compounds are being hydrogenated.

Figure 3:
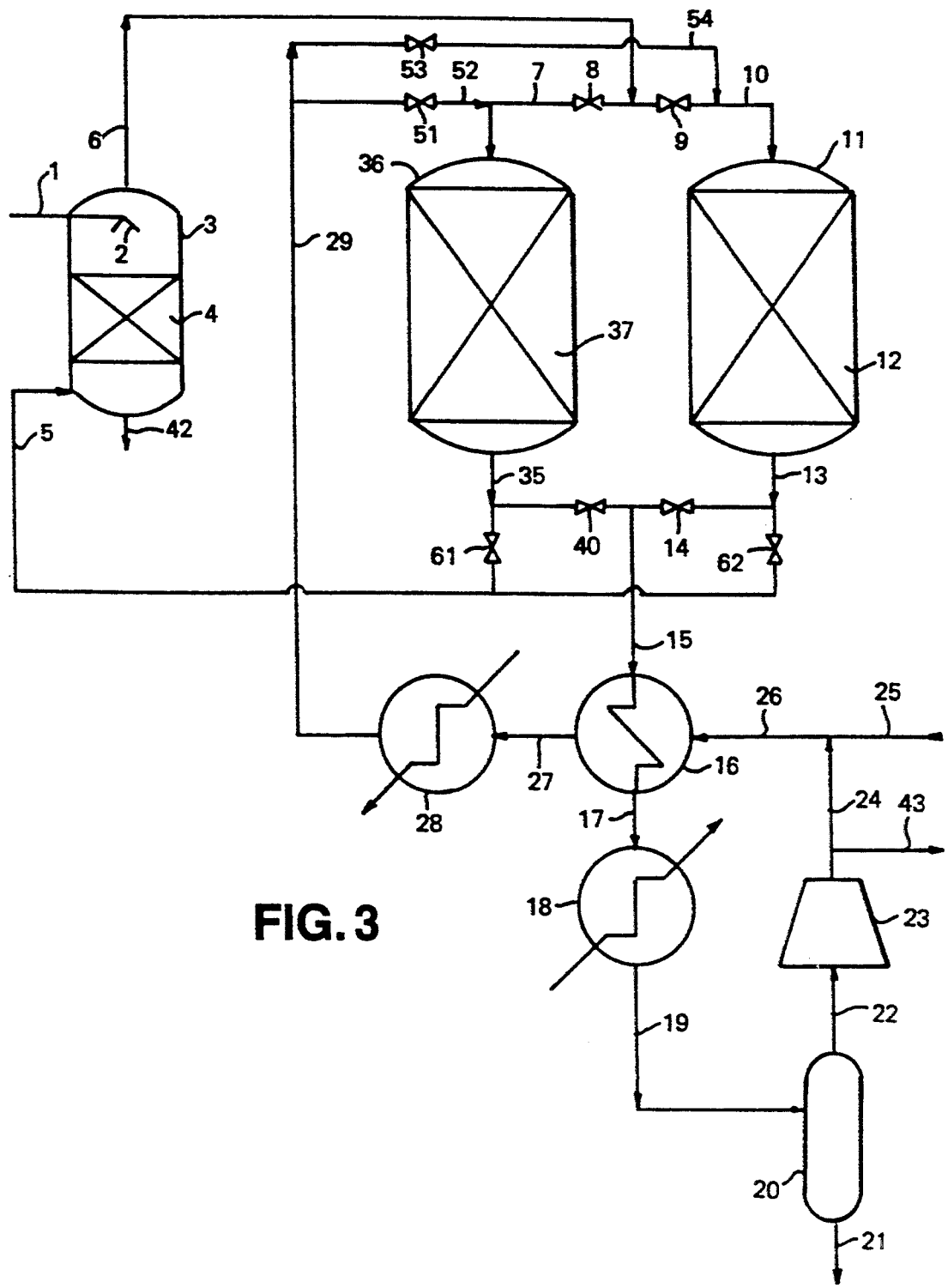

FIG. 3 illustrates a further design of hydrogenation plant in accordance with the invention. In this plant, as in the plant of FIG. 2, the direction of gas flow through each of the catalyst beds 12 and 37 during its respective reactivation mode is the same as the direction of flow of vaporous feed mixture during its on line mode. The reference numerals used in FIG. 3 indicate the same items of equipment that appear in FIG. 1 and also in FIG. 2.

In the plant of FIG. 3 the hydrogen-containing gas supplied in line 5 for vaporisation of the incoming dimethyl 1,4-cyclohexanedicarboxylate feed in line 1 is passed first through one of the catalyst beds 12 or 37 in its respective reactivation mode. Hence, when reactor 36 is in reactivation mode, most of the hot gas in line 29 is fed through valve 51 and line 52 into reactor 36 through catalyst charge 37, and passes out via line 35 and valve 61 to line 5. Valves 8 and 40 are closed and valve 53 is open only so far as is necessary to permit passage of sufficient gas into line 10 to satisfy dew point requirements. Meanwhile the vaporous feed mixture in line 6 passes through valve 9 and via line 10 into reactor 11 whose catalyst charge 12 is in on line mode. The product stream in line 13 flows through valve 14 into line 15, valve 62 being closed. When it is desired to bring catalyst charge 37 on line and to reactivate catalyst charge 12 in reactor 11, valves 8, 40 and 62 are opened, while formerly open valves 9, 14 and 61 are closed. Valve 53 is opened somewhat and the gas flow through valve 51 is reduced to the extent necessary for dew point considerations. To revert to the former condition with catalyst charge 37 being reactivated and catalyst charge 12 being on line again, the conditions of the various valves are each readjusted to its respective former condition. This procedure can be repeated one or more further times.

Figure 4:
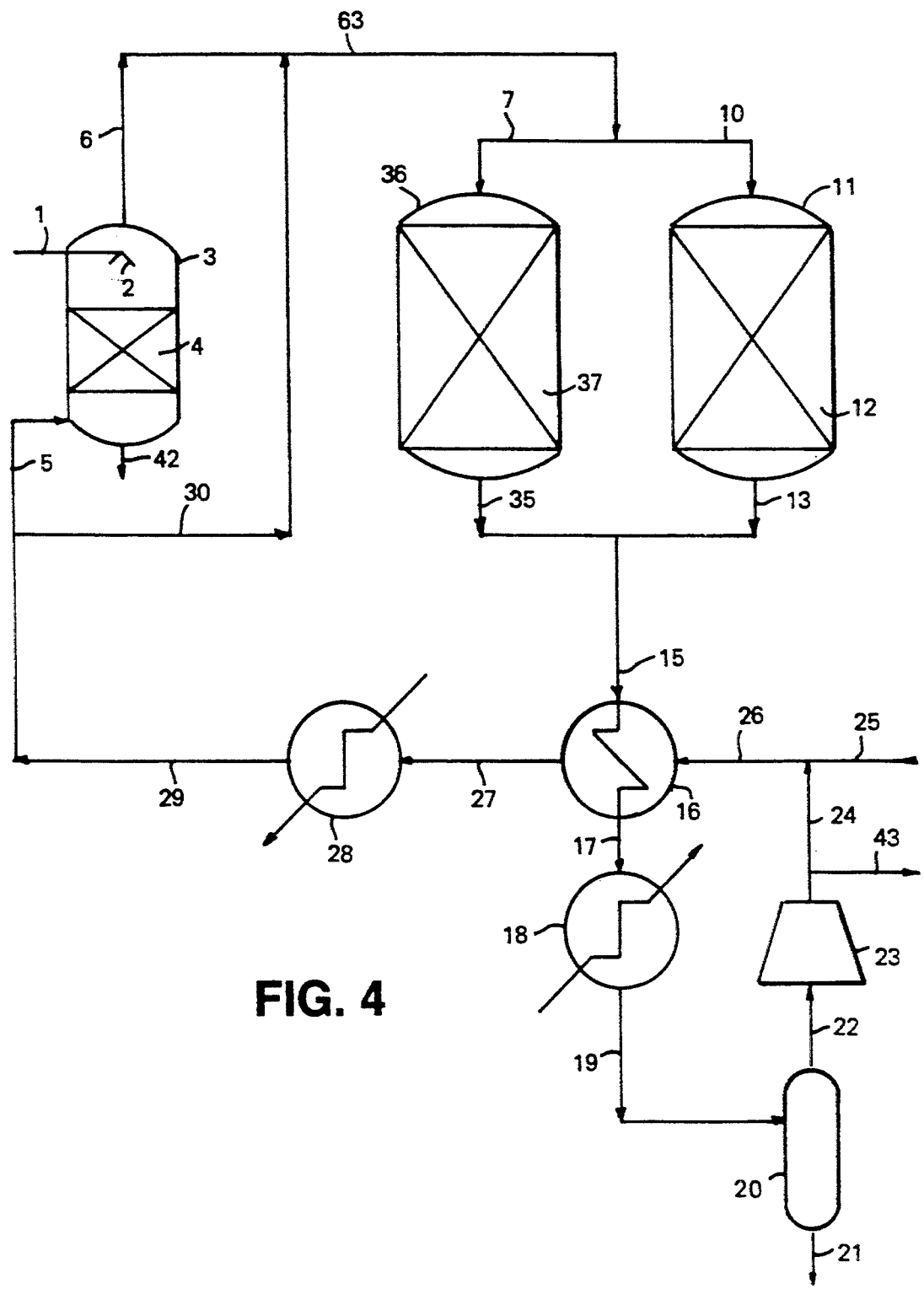

In the plant of FIG. 4 part of the hot mixture of recycle gas and make-up gas in line 29 is fed by way of line 5 to vaporiser 3 while the remainder bypasses vaporiser 3 in line 30 and is admixed with the essentially saturated vaporous hydrogen-containing stream of dimethyl cyclohexanedicarboxylate in line 6 so as to form the feed mixture in line 63 for supply to the hydrogenation step. The feed stream in line 63 can be divided and fed by way of lines 7 and 10 to hydrogenation reactors 36 and 11 which have outlet lines 35 and 13 which can be connected simultaneously to common exit line 15. Alternatively the entire vaporous stream in line 63 can be fed through one of reactors 36 and 11 only, by way of line 7 or line 10 and the product mixture collected by way of line 35 or line 13 in line 15.

At start up of the plant of FIG. 4 the hydrogenation reactors 36 and 11 are each charged with a charge of a hydrogenation catalyst precursor which is then reduced carefully following the catalyst supplier's instructions. If using the process of EP-A-0301853 to reduce a copper chromite precursor, then both beds of catalyst 37 and 12 can be reduced simultaneously. In other cases it may be expedient to reduce the beds 37 and 12 separately. After pre-reduction of the catalyst precursor hot hydrogen-containing gas is circulated through the plant. When the appropriate outlet temperatures to vaporiser vessel 3 and to reactor 36 and/or reactor 11 have been achieved the flow of dimethyl 1,4-cyclohexanedicarboxylate in line 1 is commenced.

If the procedure of WO-A-91/01961 is to be used, reactor 36 is used alone in a first phase of operation, with reactor 11 off line in a standby mode and with its catalyst bed 12 bathed with hydrogen. After a suitable period of operation during which the activity of the catalyst in bed 37 declines somewhat, the feed is switched to reactor 11 while reactor 36 is placed on standby. After a second phase of operation of the plant during which the activity of the hydrogenation catalyst in bed 12 declines, reactor 36 is brought on line again so that both reactors 36 and 11 are used simultaneously in parallel in a third phase of operation. In this way the throughput of the plant can be maintained, whilst the corresponding liquid hourly space velocity in each reactor 36 or 11 is about 50% of that prevailing during the respective first and second phases of operation of the plant. After this third period of operation the activity of the catalyst will have declined to a point at which it is desirable to shut down the plant for maintenance and to install a new catalyst charge.

The invention is further described with reference to the following Examples. The compositions of catalysts A to D used in the Examples are listed in Table I. The oxygen content of the catalyst has been excluded from the analysis in each case.

TABLE I

| Catalyst | | Composition wt % | | | | | Surface area $m^2/g$ | Density $g/cm^3$ | Pore volume $mm^3/g$ |
| --- | --- | --- | --- | --- | --- | --- | --- | --- | --- |
| | | Cu | Cr | Zn | Mn | Ba | Al | | | |
| A | PG 85/1 | 42.4 | 31.4 | <0.01 | 0.02 | 0.05 | <0.01 | 25 | 1.275 | 260 |
| B | DRD 89/21 | 57.6 | 19.0 | <0.01 | 0.09 | <0.01 | <0.01 | 28 | 1.420 | 200 |
| C | DRD 92/89 | 41.1 | 0.26 | <0.01 | 6.4 | <0.01 | 20.4 | 47.1 | 1.452 | 211 |
| D | DRD 92/92 | 34.5 | 0.02 | 43.1 | 2.2 | <0.01 | <0.01 | 70 | 1.423 | 210 |

EXAMPLE 1

Figure 5:
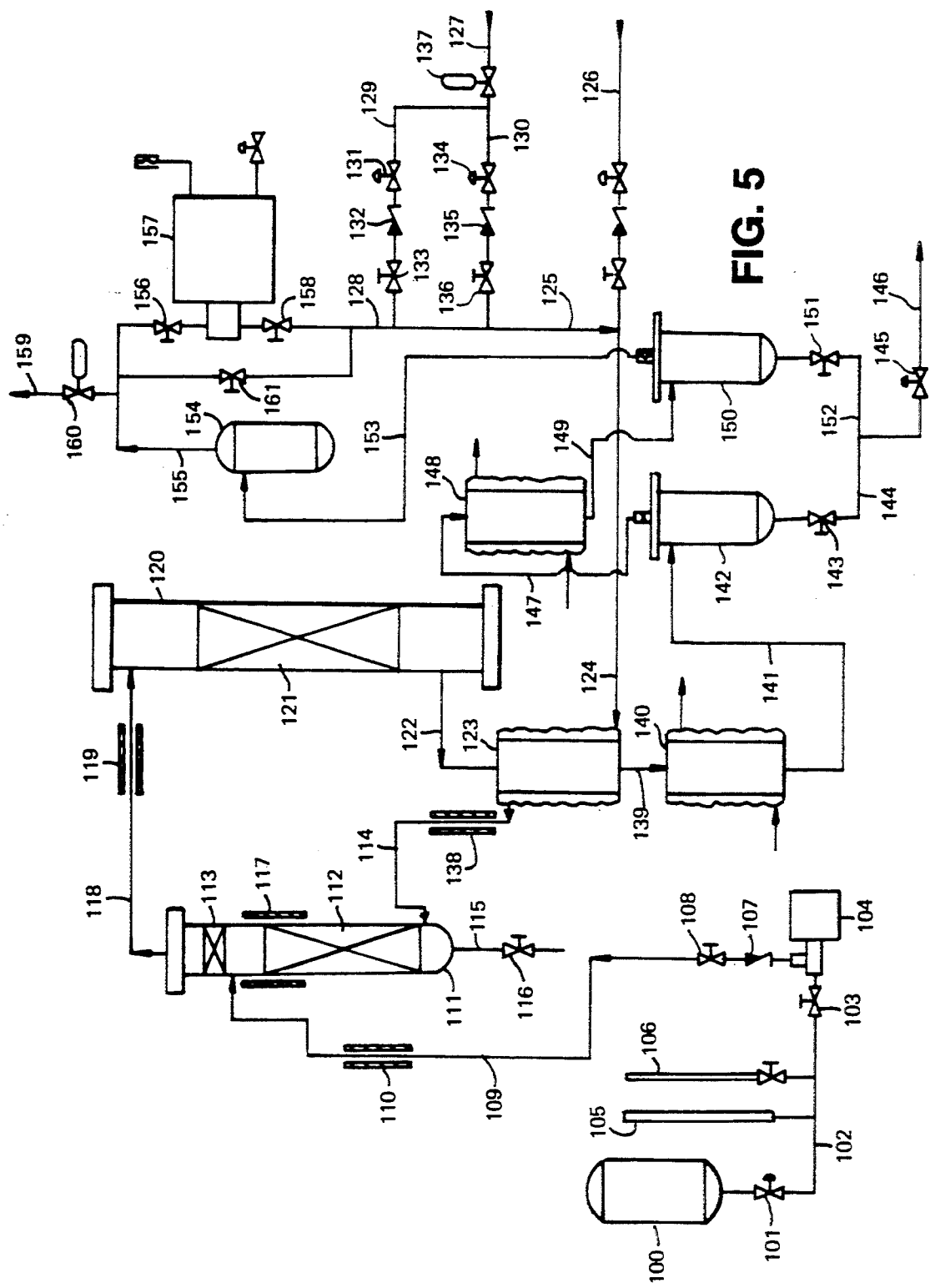
FIG. 5 is a simplified flow diagram of an experimental apparatus for production of 1,4-cyclohexanedimethanol in a single hydrogenation zone by hydrogenation of dimethyl 1,4-cyclohexanedicarboxylate.

The hydrogenation of a high purity grade of dimethyl 1,4-cyclohexanedicarboxylate was investigated using the experimental apparatus illustrated in FIG. 5.

The composition of the high purity feed was: 36.16 wt % trans-dimethyl 1,4-cyclohexanedicarboxylate, 63.26 wt % cis-dimethyl 1,4-cyclohexanedicarboxylate, 0.17% methyl hydrogen 1,4-cyclohexanedicarboxylate of formula

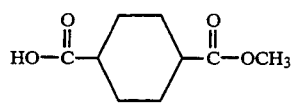

and 0.07 wt % water, with the balance being impurities.

In a commercial plant, hydrogen gas is separated from the hydrogenation product and is advantageously recycled through the hydrogenation zone. The hydrogen recycle stream will contain a quantity of methanol vapour produced by the hydrogenation of dimethyl 1,4-cyclohexanedicarboxylate. Hence, the vaporous mixture supplied to the hydrogenation zone in a commercial plant will generally contain methanol in addition to hydrogen and an unsaturated organic compound. In order that the experimental rig described hereinbelow should accurately predict the likely results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described hereinbelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In this Example and in all succeeding Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 5. An approximately 70 wt % solution of the high purity grade of dimethyl 1,4-cyclohexanedicarboxylate in methanol is fed from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6 mm × 6 mm glass rings 112. A stainless steel demister pad 113 is fitted at the top end of the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 300 ml (428.1 g) of a pelleted copper chromite hydrogenation catalyst 121. The catalyst was catalyst A of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) within insulating material around reactor 120 under the control of appropriately positioned thermocouples (not shown). The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and control valve 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of catalyst was placed in reactor 120 which was then purged with nitrogen. The catalyst charge was then reduced according to the teachings of EP-A-0301853.

High purity dimethyl 1,4-cyclohexanedicarboxylate, appropriately diluted with methanol, was then pumped to the vaporiser 111 at a rate of 75 ml/h corresponding to a liquid hourly space velocity of 0.25 h$^{-1}$. The gas:-dimethyl 1,4-cyclohexanedicarboxylate molar ratio in the vaporous mixture in line 118 was 915:1. The reactor 120 was maintained at a temperature of 220° C. and a pressure of 900 psia (62.05 bar). The hydrogenation zone was therefore operated under conditions which prevented the condensation of both dimethyl 1,4-cyclohexanedicarboxylate and the less volatile 1,4-cyclohexanedimethanol product. The temperature throughout the hydrogenation zone was above the dew point at the operating pressure.

The liquid in line 146 was analysed periodically by capillary gas chromatography using a 15 m long, 0.32 mm internal diameter fused silica column coated internally with a 0.25 82 m film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. Included amongst the compounds detected in the reaction mixture were 1,4-cyclohexanedimethanol, dimethyl 1,4-cyclohexanedicarboxylate, 4-methoxymethyl cyclohexanemethanol, di-(4-methoxymethylcyclohexylmethyl) ether, and methanol. From the results obtained it was demonstrated that dimethyl 1,4-cyclohexanedicarboxylate can be converted in excess of 99%, with a selectivity to 1,4-cyclohexanedimethanol of approximately 98.5% being obtained, the balance being minor by-products. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction. The results are listed in Table II below, together with the results from the succeeding Examples 2 to 8.

TABLE II

| Example No. | Pressure psia (bar) | Inlet Temp. °C. | Gas:DMCD molar ratio | LHSV h$^{-1}$ | DMCD conversion mol % | CHDM trans-:cis- ratio | Selectivity mol % | | | |
|---|---|---|---|---|---|---|---|---|---|---|
| | | | | | | | CHDM | BYPR | METH | DETH |
| 1 | 900 (62.05) | 220 | 915 | 0.25 | 99.95 | 3.70 | 98.35 | 1.13 | 0.33 | 0.19 |
| 2 | 900 (62.05) | 220 | 876 | 0.27 | 99.95 | 3.71 | 98.47 | 1.13 | 0.27 | 0.13 |
| 3 | 900 (62.05) | 222 | 682 | 0.43 | 99.93 | 3.65 | 98.66 | 0.94 | 0.26 | 0.14 |
| 4 | 900 (62.05) | 221 | 651 | 0.59 | 97.36 | 2.73 | 99.09 | 0.58 | 0.17 | 0.16 |
| 5 | 900 (62.05) | 240 | 356 | 0.61 | 99.64 | 3.32 | 97.99 | 1.70 | 0.24 | 0.07 |
| 6 | 900 (62.05) | 231 | 535 | 0.60 | 99.21 | 3.17 | 98.84 | 0.96 | 0.15 | 0.05 |
| 7 | 900 (62.05) | 231 | 550 | 0.40 | 99.82 | 3.47 | 98.39 | 1.26 | 0.23 | 0.12 |
| 8 | 900 (62.05) | 222 | 721 | 0.40 | 99.40 | 3.22 | 99.26 | 0.51 | 0.14 | 0.09 |

Notes to Table II:
DMCD = dimethyl 1,4-cyclohexanedicarboxylate
LHSV = liquid hourly space velocity
CHDM = cyclohexanedimethanol
BYPR = miscellaneous by-products
METH = 4-methoxymethyl cyclohexanemethanol
DETH = di-4-hydroxymethylcyclohexylmethyl ether
Gas = hydrogen containing gas containing more than 98% hydrogen

EXAMPLES 2 TO 8

Using a similar procedure to that described in Example 1 and the same feed solution, 7 further runs were carried out using the copper chromite catalyst (catalyst A in Table I). The runs were designed to investigate the effect on the hydrogenation reaction of changes in operating conditions such as temperature, pressure, LHSV and gas:ester mole ratio. In each case the vaporous mixture in contact with the catalyst was above its dew point. The results are summarised in Table II.

EXAMPLE 9

The charge of copper chromite catalyst used in Examples 1 to 8 was replaced by 150 ml (240.8 g) of DRD 89/21 (catalyst B in Table I), a copper-chromite catalyst with a Cu/Cr weight ratio of 3:1. The catalyst was activated following the procedure described in Example 1 and a methanol solution of high purity dimethyl 1,4-cyclohexanedicarboxylate was supplied to the vaporiser 111 at a rate of 60 ml/h corresponding to liquid hourly space velocity of 0.40 h$^{-1}$. The inlet temperature to the hydrogenation zone was 221° C., i.e. above the dew point of the vaporous mixture.

A conversion of 99.52% of dimethyl-1,4-cyclohexanedicarboxylate was obtained. Detailed results are shown in Table III below, as well as the results obtained in Examples 10 to 23. The notes to Table II apply also to Table III.

TABLE III

| Example No. | Pressure psia (bar) | Inlet Temp. °C. | Gas:DMCD mol ratio | LHSV h$^{-1}$ | DMCD conversion mol % | CHDM trans-:cis- ratio | Selectivity mol % | | | |
|---|---|---|---|---|---|---|---|---|---|---|
| | | | | | | | CHDM | BYPR | METH | DETH |
| 9 | 690 (47.57) | 221 | 543 | 0.40 | 99.52 | 3.39 | 98.92 | 0.70 | 0.21 | 0.17 |
| 10 | 915 (63.09) | 221 | 773 | 0.40 | 99.66 | 3.27 | 99.03 | 0.65 | 0.20 | 0.12 |
| 11 | 450 (31.03) | 220 | 346 | 0.41 | 98.23 | 3.37 | 98.95 | 0.78 | 0.17 | 0.10 |
| 12 | 900 (62.05) | 219 | 684 | 0.41 | 99.70 | 3.41 | 99.08 | 0.65 | 0.19 | 0.08 |
| 13 | 900 (62.05) | 220 | 697 | 0.41 | 99.57 | 3.00 | 98.29 | 0.90 | 0.72 | 0.09 |
| 14 | 900 (62.05) | 220 | 695 | 0.62 | 98.21 | 2.47 | 99.01 | 0.64 | 0.25 | 0.10 |
| 15 | 901 (62.12) | 221 | 659 | 0.42 | 98.71 | 2.61 | 96.98 | 2.77 | 0.18 | 0.07 |
| 16 | 899 (61.98) | 221 | 725 | 0.58 | 93.99 | 2.00 | 96.84 | 2.93 | 0.14 | 0.09 |

TABLE III-continued

| Example No. | Pressure psia (bar) | Inlet Temp. °C. | Gas:DMCD mol ratio | LHSV h$^{-1}$ | DMCD conversion mol % | CHDM trans-:cis- ratio | Selectivity mol % | | | |
|---|---|---|---|---|---|---|---|---|---|---|
| | | | | | | | CHDM | BYPR | METH | DETH |
| 17 | 901 (62.12) | 220 | 720 | 0.40 | 98.30 | 2.45 | 96.95 | 2.79 | 0.16 | 0.10 |
| 18 | 900 (62.05) | 240 | 362 | 0.40 | 99.82 | 3.31 | 95.59 | 4.03 | 0.31 | 0.07 |
| 19 | 903 (62.26) | 240 | 364 | 0.60 | 98.75 | 2.93 | 95.94 | 3.71 | 0.23 | 0.12 |
| 20 | 900 (62.05) | 220 | 691 | 0.42 | 97.53 | 2.35 | 96.89 | 2.84 | 0.14 | 0.13 |
| 21 | 900 (62.05) | 220 | 720 | 0.40 | 97.85 | 2.39 | 96.93 | 2.81 | 0.14 | 0.12 |
| 22 | 901 (62.12) | 221 | 530 | 0.41 | 98.20 | 2.48 | 96.93 | 2.81 | 0.14 | 0.12 |
| 23 | 900 (62.05) | 224 | 446 | 0.40 | 98.92 | 2.76 | 96.80 | 2.84 | 0.16 | 0.20 |

EXAMPLES 10 TO 14

The effect on dimethyl 1,4-cyclohexanedicarboxylate hydrogenation of altering the operating conditions described in Example 9 was investigated in 5 further experiments. Detailed results are shown in Table III. In each of Examples 10 to 14 the vaporous mixture in contact with the catalyst was above its dew point.

EXAMPLES 15 to 23

The high purity dimethyl 1,4-cyclohexanedicarboxylate supplied to the hydrogenation zone in Examples 1 to 14 was replaced with a technical grade feed. The composition of the technical grade feed was: 33.95 wt % trans-dimethyl 1,4-cyclohexanedicarboxylate, 61.60 wt % cis-dimethyl 1,4-cyclohexanedicarboxylate, 1.59 wt % methyl hydrogen 1,4-cyclohexanedicarboxylate, 0.07 wt % water and 2.79 wt % of high boiling impurities including di-4-hydroxymethylcyclohexyl methyl ether. The feed was supplemented with methanol as described in Example 1. Detailed results are shown in Table III. In each of these Examples the vaporous mixture in contact with the catalyst was above its dew point.

EXAMPLE 24

The charge of copper chromite catalyst used in Examples 9 to 23 was replaced by 300 ml of DRD 92/89 (catalyst C in Table I), a non-chromium catalyst containing copper, manganese and alumina. The catalyst was activated by a procedure analogous to that described in Example 1 and high purity dimethyl 1,4-cyclohexanedicarboxylate was supplied as a methanol solution to the vaporiser 111 at a rate of 123 ml/h corresponding to a liquid hourly space velocity of 0.42 h$^{-1}$. The gas:ester molar ratio of the vaporous mixture reaching the hydrogenation zone was 703:1 and the hydrogenation zone was maintained at 900 psia (62.05) bar with an inlet temperature of 220° C., i.e. 10° C. above the dew point of the vaporous feed mixture at this pressure.

A dimethyl 1,4-cyclohexanedicarboxylate conversion of 99.78% was obtained. Detailed results are shown in Table IV below. The notes to Table II apply also to Table IV.

EXAMPLE 25

The effect on hydrogenation of high purity dimethyl 1,4-cyclohexanedicarboxylate of altering the operating conditions, specifically the LHSV described in Example 24, was investigated in a further experiment. Detailed results are shown in Table IV. Again the dimethyl 1,4-cyclohexanedicarboxylate was supplied to the vaporiser as a solution in methanol. The vaporous mixture in contact with the catalyst was about 10° C. above its dew point at the operating pressure.

EXAMPLES 26 TO 32

The high purity dimethyl 1,4-cyclohexanedicarboxylate feed of Examples 24 and 25 was replaced with a technical grade feed whose composition has already been described in Examples 15 to 23. The effect on hydrogenation of this technical grade feed of altering the operating conditions described in Example 24 was investigated in 7 further experiments. Detailed results are shown in Table IV; the notes to Table II apply also to Table IV. In each of Examples 26 to 32 the vaporous mixture in contact with the catalyst was above its dew point.

TABLE IV

| Example No. | Pressure psia (bar) | Inlet Temp. °C. | Gas:DMCD mol ratio | LHSV h$^{-1}$ | DMCD conversion mol % | CHDM trans-:cis- ratio | Selectivity mol % | | | |
|---|---|---|---|---|---|---|---|---|---|---|
| | | | | | | | CHDM | BYPR | METH | DETH |
| 24 | 900 (62.04) | 220 | 703 | 0.42 | 99.78 | 3.47 | 98.18 | 0.52 | 0.11 | 0.19 |
| 25 | 900 (62.04) | 220 | 691 | 0.60 | 99.19 | 3.02 | 99.29 | 0.44 | 0.10 | 0.17 |
| 26 | 900 (62.04) | 242 | 363 | 0.99 | 99.55 | 3.29 | 98.23 | 1.54 | 0.14 | 0.09 |
| 27 | 900 (62.04) | 242 | 378 | 1.20 | 99.20 | 3.20 | 98.17 | 1.48 | 0.13 | 0.22 |
| 28 | 900 (62.04) | 219 | 684 | 0.41 | 99.75 | 3.41 | 97.13 | 2.67 | 0.08 | 0.12 |
| 29 | 903 (62.24) | 218 | 690 | 0.41 | 99.73 | 3.37 | 97.14 | 2.68 | 0.08 | 0.10 |
| 30 | 900 (62.04) | 220 | 684 | 0.62 | 97.61 | 2.61 | 97.53 | 2.27 | 0.06 | 0.14 |
| 31 | 906 (62.52) | 220 | 731 | 0.49 | 98.10 | 2.66 | 97.65 | 2.26 | 0.09 | 0.00 |
| 32 | 909 (62.66) | 220 | 495 | 0.50 | 99.57 | 3.12 | 96.92 | 2.94 | 0.07 | 0.07 |

EXAMPLES 33 TO 35

In an experiment to determine the vapour phase equilibrium trans-:cis- 1,4-cyclohexanedimethanol product ratio, an experimental apparatus of the type described in Example 1 was packed with 250 ml of catalyst C of Table I and supplied with a feed of a hydrogenation product of dimethyl 1,4-cyclohexanedicarboxylate having the following composition: 48.6 wt % methanol, 1.4 wt % dimethyl 1,4-cyclohexanedicarboxylate, 36.2 wt % trans-1,4-cyclohexanedimethanol, 10.4 wt % cis-1,4-cyclohexanedimethanol, 0.11 wt % 4-methoxymethyl cyclohexanemethanol, 0.42 wt % di-(4-hydroxymethyl-cyclohexylmethyl) ether, 0.5 wt % water and 2.31 wt % of other by-products. This hydrogenation product thus had a trans:cis- 1,4-cyclohexanedimethanol ratio of 3.48:1. The process parameters for Example 33 were as set out in Table V. The product from Example 33 was then passed through the reactor of a second experimental rig of the type described in Example 1 which was packed with 250 ml of catalyst C of Table I. The process parameters and product trans-:cid- ratio for this second run are shown in Example 34 in Table VI. The product mixture from Example 34 was fed through a third experimental rig of the type described in Example 1, again packed with 250 ml of catalyst C of Table I. The trans-:cis- 1,4-cyclohexanedimethanol product ratio resulting from this third run, Example 35, can be seen to have stabilised at around 3.84:1, the vapour phase equilibrium value.

TABLE V

| Example No. | 33 | 34 | 35 |
| --- | --- | --- | --- |
| Pressure psia (bar) | 900 (62.05) | 900 (62.05) | 900 (62.05) |
| Inlet temp. (°C.) | 221 | 221 | 220 |
| H$_2$:DMCD ratio | 571 | 570 | 570 |
| Exit temp. (°C.) | 221 | 221 | 220 |
| Dew point (°C.) | 213 | 213 | 213 |
| Residence time (sec) | 4.6 | 9.3 | 9.3 |
| LHSV (h$^{-1}$) | 0.37 | 0.19 | 0.19 |
| trans-/cis-CHDM | 3.77 | 3.84 | 3.84 |
| DMCD conversion (%) | 99.99 | 99.99 | 100.00 |

EXAMPLES 36 AND 37

The procedure of Example 1 is repeated using, in place of dimethyl 1,4-cyclohexanedicarboxylate, dimethyl 1,2-cyclohexanedicarboxylate and dimethyl 1,3-cyclohexanedicarboxylate respectively. Similar results are obtained.

EXAMPLE 38

The procedure of Example 1 is repeated using in place of catalyst A an equal volume of catalyst D. Similar results are observed.

We claim

1. A process for the production of cyclohexanedimethanol having a trans-:cis-isomer ratio greater than about 1:1 by hydrogenation of dialkyl cyclohexanedicarboxylate having a trans-:cis-isomer ratio less than about 1:1 which comprises:
   (a) providing a hydrogenation zone containing a charge of a granular heterogenous ester hydrogenation catalyst selected from copper-containing catalysts and Group VIII metal-containing catalysts;
   (b) supplying to the hydrogenation zone a vaporous feed stream containing hydrogen and a hydrogenatable material comprising dialkyl cyclohexanedicarboxylate at an inlet temperature which is above the dew point of the mixture;
   (c) maintaining the hydrogenation zone at a combination of a temperature of from about 150° C. to about 350° C. and a pressure of from about 150 psia (about 10.34 bar) to about 2000 psia (about 137.90 bar);
   (d) passing the vaporous feed stream through the hydrogenation zone; and
   (e) recovering from the hydrogenation zone a product stream containing cyclohexanedimethanol having a trans-:cis-isomer ratio greater than 1:1;
wherein the dialkyl cyclohexanedicarboxylate is selected from di-(C$_1$ to C$_4$ alkyl) cyclohexanedicarboxylates.

2. A process according to claim 1, in which the dialkyl cyclohexanedicarboxylate is dimethyl 1,4-cyclohexanedicarboxylate.

3. A process according to claim 2, in which the dialkyl cyclohexanedicarboxylate is cis-dimethyl 1,4-cyclohexanedicarboxylate.

4. A process according to any claim 3, in which the dialkyl cyclohexanedicarboxylate comprises a mixture of the cis- and trans-isomers of dimethyl 1,4-cyclohexanedicarboxylate in which the molar ratio of trans-dimethyl cyclohexanedicarboxylate to cis-dimethyl cyclohexanedicarboxylate is in the range of from about 0.01:1 to about 1:1.

5. A process according to claim 4, in which the dialkyl cyclohexanedicarboxylate comprises a mixture of the cis- and trans-isomers of dimethyl 1,4-cyclohexanedicarboxylate in which the molar ratio of trans-dimethyl cyclohexanedicarboxylate to cis-dimethyl cyclohexanedicarboxylate is in the range of from about 0.05:1 to about 1:1.

6. A process according to claim 5, in which the dialkyl cyclohexanedicarboxylate comprises a mixture of the cis- and trans-isomers of dimethyl 1,4-cyclohexanedicarboxylate in which the molar ratio of trans-dimethyl cyclohexanedicarboxylate to cis-dimethyl cyclohexanedicarboxylate is in the range of from about 0.5:1 to about 0.6:1.

7. A process according to claim 1, in which the hydrogen-containing gas:dialkyl cyclohexanedicarboxylate mole ratio in the vaporous mixture is in the range of from about 200:1 to about 1000:1.

8. A process according to claim 1, in which the feed temperature to the hydrogenation zone is in the range of from about 150° C. to about 300° C.

9. A process according to claim 8, in which the feed temperature to the hydrogenation zone is in the range of from about 200° C. to about 260° C.

10. A process according to claim 8, in which the feed pressure to the hydrogenation zone is in the range of from about 450 psia (about 31.03 bar) to about 1000 psia (about 68.95 bar).

11. A process according to claim 8, in which the catalyst is selected from reduced manganese promoted copper catalysts, reduced copper chromite catalysts, reduced promoted copper chromite catalysts, supported palladium/zinc catalysts, chemically mixed copper-titanium catalysts, platinum catalysts and palladium catalysts.

12. A process according to claim 11, in which the catalyst is selected from the reduced forms of copper chromite, promoted copper chromite, and manganese promoted copper catalysts.

13. A process according to claim 12, in which the catalyst comprises not more than about 15% by weight of at least one promoter selected from barium, manganese, and mixtures thereof.

14. A process according to claim 8, in which the vaporous feed stream is supplied at a rate corresponding to a liquid hourly space velocity of the dialkyl cyclohexanedicarboxylate of from about 0.05 to about 4.0 h$^{-1}$.

15. A process according to claim 1, in which the dialkyl cyclohexanedicarboxylate is dimethyl 1,4-cyclohexanedicarboxylate and in which the product stream of step (e) comprises a 1,4-cyclohexanedimethanol product having a trans.-:cis-isomer ratio of from about 2:1 to about 3.84:1.

16. A process according to claim 15, in which the product stream of step (e) comprises a 1,4-cyclohexanedimethanol product having a trans-:cis-isomer ratio of from about 2.6:1 to about 3.84:1.

17. A process according to claim 16, in which the product stream of step (e) comprises a 1,4-cyclohexanedimethanol product having a trans-:cis-isomer ratio of from about 3.1:1 to about 3.84:1.

18. A process according to claim 1, in which the vaporous mixture comprises dimethyl 1,3-cyclohexanedicarboxylate.

19. A process according to claim 1, in which the vaporous mixture comprises dimethyl 1,2-cyclohexanedicarboxylate.

20. A vapor phase process for the production of cyclohexanedimethanol by hydrogenation of dimethyl cyclohexanedicarboxylate which comprises:
(a) providing a hydrogenation zone containing a charge of a granular heterogenous ester hydrogenation catalyst selected from reduced copper chromite catalysts wherein the Cu:Cr weight ratio is from about 0.1:1 to about 4:1; reduced, copper chromite catalysts wherein the Cu:Cr weight ratio is from about 0.1:1 to about 4:1 promoted with from about 0.1% by weight up to 15% by weight of barium, manganese or a mixture of barium and manganese; or reduced manganese promoted copper catalysts wherein the Cu:Mn weight ratio is from about 2:1 to about 10:1;
(b) supplying to the hydrogenation zone a vaporous feed stream containing hydrogen and dimethyl cyclohexanedicarboxylate at an inlet temperature which is at or above the dew point of the mixture, wherein the dimethyl cyclohexanedicarboxylate is supplied to the hydrogenation zone at a rate corresponding to a liquid hourly space velocity of from 0.05 to about 4.0 h$^{-1}$;
(c) maintaining the hydrogenation zone at a combination of a temperature of from about 150° C. to about 300° C. and a pressure of from about 150 psia (about 10.34 bar) to about 2000 psia (about 137.90 bar) which maintains both the dimethyl cyclohexanedicarboxylate reactant and the cyclohexanedimethanol product in the vapour phase; and
(d) recovering from the hydrogenation zone a vaporous cyclohexanedimethanol product wherein the trans-:cis-isomer ratio of the cyclohexanedimethanol product is in the range of from about 2:1 to about 3.8:1.

21. A process according to claim 20, in which the pressure within the hydrogenation zone is in the range of about 450 psia (about 31.03 bar) up to about 1000 psia (about 68.95 bar).

22. A process according to claim 21, in which the heterogeneous ester hydrogenation catalyst is a manganese promoted copper catalyst having a Cu:Mn weight ratio of from about 2:1 to about 10:1.

23. A vapor phase process for the production of 1,4-cyclohexanedimethanol by hydrogenation of dimethyl 1,4-cyclohexanedicarboxylate which comprises:
(a) providing a hydrogenation zone containing a charge of a granular heterogenous ester hydrogenation catalyst selected from reduced copper chromite catalysts wherein the Cu:Cr weight ratio is from about 0.1:1 to about 4:1; reduced, copper chromite catalysts wherein the Cu:Cr weight ratio is from about 0.1:1 to about 4:1 promoted with from about 0.1% by weight up to 15% by weight of barium, manganese or a mixture of barium and manganese; or reduced manganese promoted copper catalysts wherein the Cu:Mn weight ratio is from about 2:1 to about 10:1;
(b) supplying to the hydrogenation zone a vaporous feed stream containing hydrogen and dimethyl 1,4-cyclohexanedicarboxylate at an inlet temperature which is at or above the dew point of the mixture, wherein the dimethyl 1,4-cyclohexanedicarboxylate is supplied to the hydrogenation zone at a rate corresponding to a liquid hourly space velocity of from 0.2 to about 1.0 h$^{-1}$;
(c) maintaining the hydrogenation zone at a combination of a temperature of from about 210° C. to about 260° C. and a pressure of from about 450 psia (about 31.03 bar) to about 1000 psia (about 68.95 bar) which maintains both the dimethyl 1,4-cyclohexanedicarboxylate reactant and the 1,4-cyclohexanedimethanol product in the vapour phase; and
(d) recovering from the hydrogenation zone a vaporous 1,4-cyclohexanedimethanol product wherein the trans-:cis-isomer ratio of the cyclohexanedimethanol product is in the range of from about 2.6:1 to about 3.8:1.

* * * * *